United States Patent [19]

Pietzuch

[11] 4,253,336
[45] Mar. 3, 1981

[54] VEHICLE EXHAUST EMISSION TESTING ADAPTER

[76] Inventor: Edward E. Pietzuch, 4307 Joan Pl., Cincinnati, Ohio 45227

[21] Appl. No.: 21,933

[22] Filed: Mar. 19, 1979

[51] Int. Cl.³ .............................................. G01N 1/22
[52] U.S. Cl. ................................................. 73/422 R
[58] Field of Search ........... 73/421.5 R, 422 R, 421 B

[56] References Cited

U.S. PATENT DOCUMENTS

| 2,226,097 | 12/1940 | Happel et al. ..................... 73/422 R |
| 3,793,887 | 2/1974 | Anderson et al. .............. 73/421.5 R |
| 3,930,413 | 1/1976 | Laird .................................. 73/422 R |

Primary Examiner—S. Clement Swisher
Attorney, Agent, or Firm—Frost & Jacobs

[57] ABSTRACT

An adapter for use with vehicle exhaust emission testing apparatus of the type utilizing an elongated tube-like sampling probe, the adapter including a tube-like body member having one end connected to the vehicle exhaust and the other end exhausting gases from the test area. A smaller tube-like conduit connected to the body member contains a diaphram-like resilient valve permitting entrance of the sampling probe into the adapter with minimal loss of exhaust gas.

10 Claims, 3 Drawing Figures

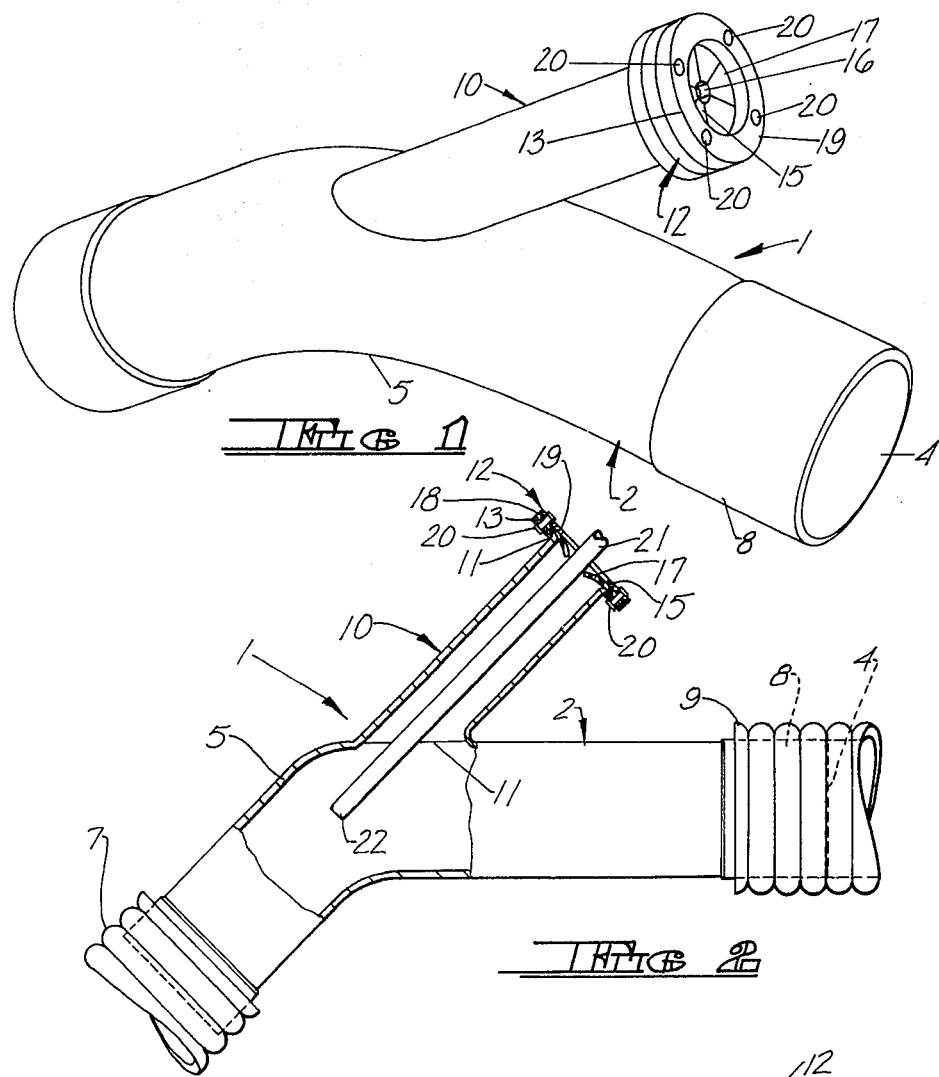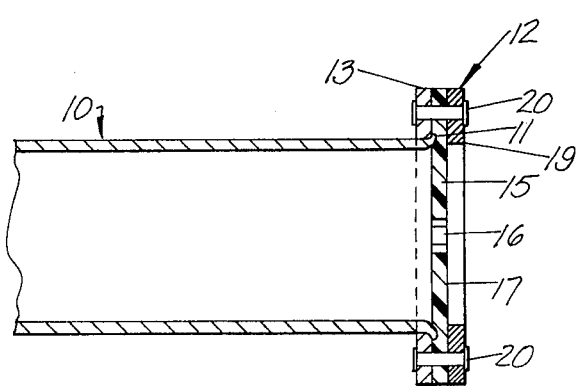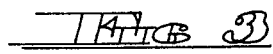

VEHICLE EXHAUST EMISSION TESTING ADAPTER

BRIEF SUMMARY OF THE INVENTION

In an attempt to reduce atmospheric pollutants caused by vehicular emissions, various types of exhaust sampling devices have been proposed for providing a quantitative and qualitative measure of the polluting materials emerging from the exhaust of vehicles powered by internal combustion engines. One common type of emission testing device includes an elongated tube-like sampling probe which is inserted into the exhaust pipe of the vehicle under test while the vehicle's engine is running. Exhaust gases traveling through the exhaust pipe enter the sampling probe and are forced, either by the pressure associated with the vehicle exhaust or by separate pumping means, to a suitable gas analyzer system.

Since such emission testing often is carried out in a closed garage or service bay, it has been found that an unhealthful level of exhaust gases is produced during the test unless adequate measures are taken to ventilate the test area. In most service areas where such tests are conducted, it is not feasible to provide the exchange of air required to insure safety for workers in the area. This is particularly true in colder weather when a window or service door cannot be left open to admit fresh air.

One approach to the problem involves connecting one end of a flexible hose to the vehicle exhaust pipe and permitting the other end of the flexible hose to extend outside of the service area. However, when the exhaust emission test is to be performed, the hose must be removed so that the sample probe can be inserted into the exhaust pipe. Such a maneuver, even if for a brief period of time, permits excessive amounts of exhaust gases to accumulate in the service area. Since such gases are not easily flushed from the service area, they may accumulate to dangerous levels after several vehicles have been tested.

The vehicle exhaust emission testing adapter of the present invention permits conventional exhaust testing as described hereinabove while minimizing escape of dangerous exhaust gases from the vehicle into the working area. In a preferred embodiment, the adapter comprises a short dog leg-shaped hollow tube-like body member having each end configured to be connected to a flexible hose of the type commonly used in vehicle exhaust removal operations. The opposite end of the flexible hose attached to the inlet end of the body member is connected to the exhaust pipe of the vehicle under test. The free end of the flexible hose connected to the outlet end of the body member extends outside of the service area so as to conduct exhaust fumes and gases away from those working in the service area.

A second smaller tube-like conduit extends outwardly at an oblique angle from the side of the body member coaxial with the inlet end of the body member so as to divide gas flow from the vehicle exhaust between the smaller conduit and the main body member. The outermost end of the side conduit contains a resilient segmented valve-like orifice which is normally substantially closed to prevent escape of exhaust gases from the orifice. When the emission testing operation is to commence, the tester sampling probe is inserted through the resilient orifice such that the tip of the sampling probe extends into the inlet end of the adapter. The resilient orifice is dimensioned to provide a relatively gas-tight seal around the outer periphery of the sampling probe, thereby preventing escape of exhaust gas into the working area during the testing operation. When the emission test has been completed, the sample probe is withdrawn from the resilient orifice, which automatically closes to prevent escape of exhaust gas. Consequently, the entire emission testing operation can be performed without the need to remove the exhaust hose from the vehicle exhaust as is presently the case.

BRIEF DESCRIPTION OF THE DRAWING

FIG. 1 is a perspective view of the vehicle exhaust emission testing adapter of the present invention.

FIG. 2 is a fragmentary side elevation view, partly in cross section, of the testing adapter of the present invention with the sampling probe in place.

FIG. 3 is a fragmentary side elevation view partially in cross section of the testing adapter of the present invention with the sampling probe removed.

DETAILED DESCRIPTION

FIG. 1 illustrates the vehicle exhaust emission testing adapter, shown generally at 1, of the present invention. The adapter comprises a dog leg-shaped hollow tube-like body member 2 having an inlet end 3 and an outlet end 4. In a preferred embodiment, bend 5 in body member 2 has been positioned approximately one third the distance of the body member from inlet end 3 at an angle of approximately 30°. This bend facilitates positioning the testing sample probe within adapter 1 as will be explained in more detail hereinafter.

As best shown in FIG. 2, inlet end 3 is slightly swedged as at 6 to accept a flexible hose 7. The other end (not shown) of flexible hose 7 is shaped over the end of the exhaust pipe of the vehicle under test. The outlet end 4 of body member 2 is also slightly swedged as at 8 so as to form a tight fit with flexible hose 9 as is best shown in FIG. 2. The remaining end (not shown) of flexible hose 9 would normally extend outside of the service area for safely exhausting combustion gases. It will be observed that the connecting portions 6 and 8 of adapter 1 permit their associated flexible hoses to be easily coupled and uncoupled to the adapter as required, while maintaining a gas-tight seal. It is preferred that flexible hoses 7 and 9 be constructed of a resilient material such as rubber, plastic or the like, to resist possible damage when inadvertently passed over by a vehicle.

A second small tube-like conduit, shown generally at 10, extends outwardly at an oblique angle from the surface of body member 2 so as to divide gas flow from the vehicle exhaust between main body member 2 and smaller conduit 10. Conduit 10 may be formed as an integral part of body member 2, or may form a separate part connected to main body member 2 by welding or the like. In general, conduit 10 will have an inside diameter slightly greater than the maximum outside diameter of the sampling probe to be used with the test adapter.

The innermost end of conduit 10 is opened as at 11 and communicates with the hollow interior of body member 2. The outermost end of conduit 10 is flared outwardly as at 11 to provide an attachment surface for the valve-like orifice shown generally at 12. Valve-like orifice 12 comprises an inner annular ring 13 containing an aperture 14 of slightly greater diameter than the outside diameter of conduit 10, such that annular ring 13 may be positioned over conduit 10 inwardly of flange 11. Positioned adjacent annular ring 13 on the outside of flange 11 is a substantially circular resilient segmented valve member 15. Valve member 15 consists of a plate-like diaphram, which may be constructed of any resilient material such as rubber, plastic or the like, and contains a central substantially circular opening 16 which facilitates the entrance of the sampling probe into the adapter as will be explained in more detail hereinafter, while preventing escape of substantial quantities of exhaust gases. Valve member 15 is further made up of a plurality of radially extending flexible segments, one of which is shown at 17, which extend from central opening 16 outwardly a distance approximating the diameter of conduit 10. The outermost flange portion 18 of valve member 15 rests against and is supported by the outermost surface of annular ring 13.

A second annular ring 19 is positioned outwardly from valve member 15 so as to hold the valve member in place. Annular ring 13, valve member 15 and annular ring 19 are held in place by rivets 20 or the like.

As is best shown in FIG. 3, resilient segments 17 of valve member 15 are normally unbiased and extend so as to seal the exit from conduit 10 against the escape of exhaust gases. However, when the sampling probe 21 is inserted through opening 16 such that it extends through conduit 10 into the inlet end of the adapter, the valve segments 17 are biased inwardly so as to press against the outside surface of the probe and prevent escape of exhaust gases. As best shown in FIG. 2, in a preferred embodiment, the inlet end of body member 2 and conduit 10 are substantially coaxial so that the tip 22 of probe 21 is in line with exhaust gases entering the inlet end of the adapter. This feature becomes particularly important when the testing apparatus used with the adapter relies on the force of the exhaust gas, rather than an external pump, to carry the gas to the associated gas analyzer. When the testing operation is completed, and probe 21 is withdrawn from the adapter, the resilient valve member segments 17 return to their normal unbiased position as shown in FIG. 3.

It will be understood that various changes in the details, materials, steps and arrangments of parts, which have been hereindescribed and illustrated in order to explain the nature of the invention, may be made by those skilled in the art within the principal and scope of the invention as expressed in the appended claims. For example, valve member 15 may be constructed of a heat resistant resilient material in order to extend the life of this member. Body member 2 and conduit 10 may be constructed of any type of suitable metal, or may be constructed of a resilient material able to withstand heavy use. It will be appreciated that locating valve member 15 at a location removed from the hot exhaust gases passing through body member 2 substantially reduces the temperature rise experienced by valve member 15 and contributes to extended life of this member. Furthermore, in constructions where conduit 10 is fabricated from a metalic or other heat conducting material, heat lost from this member also serves to maintain low operating temperatures at valve member 15. In situations where temperature rise at valve member 15 is not a problem, the entire valve member could be attached directly to the outer surface of body member 2, thus eliminating conduit 10 altogether. Finally, while slip couplings have been illustrated at the inlet and outlet ends of body member 2, other types of couplings, such as screw, bayonnet, etc. could be utilized as required.

The embodiments of the invention in which an exclusive property or privilege is claimed are as follows:

1. An adapter for use with vehicle exhaust emission testing apparatus of the type having an elongated tube-like sampling probe, said adapter comprising a hollow tube-like body member having an inlet end and an outlet end, means located at said inlet end of said member for connecting said adapter to the exhaust of a vehicle to be tested, means located at said outlet end of said member for exhausting exhaust gases from said adapter, and valve means connected to said body member, said valve means having a normally closed position for preventing escape of exhaust gases from said valve means, said valve means being configured to permit entrance of said sampling probe into said adapter while preventing escape of exhaust gases from said valve means.

2. The adapter according to claim 1 wherein said valve means comprises a resilient diaphram-like valve member.

3. The adapter according to claim 1 wherein said valve means comprises a plurality of radially extending resilient segments.

4. The adapter according to claim 3 wherein said segments form an opening at their central juncture.

5. The adapter according to claim 1 including a hollow duct-like conduit extending outwardly from said body member, the interior of said conduit communicating with the interior of said body member, said valve means being positioned on the outermost end of said conduit.

6. The adapter according to claim 5 wherein said conduit and said inlet end of said adapter are coaxial.

7. The adapter according to claim 5 wherein said conduit is positioned at an angle of less than 90° with respect to said body member.

8. The adapter according to claim 5 wherein said conduit is constructed of a heat conducting material that operates to conduct heat away from said valve means.

9. The adapter according to claim 1 wherein said connecting means and said exhausting means are configured to connect said adapter to flexible exhaust hoses.

10. The adapter according to claim 1 wherein said adapter includes a first hose member having one end attached to said connecting means for connecting said adapter to a vehicle exhaust, and a second hose member having one end attached to said exhausting means for conducting exhaust gases away from the vehicle.

* * * * *